United States Patent [19]

Ebert et al.

[11] Patent Number: 5,662,925

[45] Date of Patent: Sep. 2, 1997

[54] TRANSDERMAL DELIVERY SYSTEM WITH ADHESIVE OVERLAY AND PEEL SEAL DISC

[75] Inventors: Charles D. Ebert; Werner Heiber; William R. Good; Srinivasan Venkateshwaran, all of Salt Lake City, Utah

[73] Assignee: TheraTech, Inc., Salt Lake City, Utah

[21] Appl. No.: 638,440

[22] Filed: Apr. 26, 1996

Related U.S. Application Data

[63] Continuation of Ser. No. 361,800, Dec. 21, 1994, abandoned.

[51] Int. Cl.$^6$ ........................................ A61L 25/00
[52] U.S. Cl. ........................ 424/447; 424/448; 424/449; 602/48; 602/50; 602/51; 602/52; 602/54; 602/56; 602/58; 604/304
[58] Field of Search .......................... 424/447, 448, 424/449; 602/48, 50, 51, 52, 54, 56, 58; 604/304

[56] References Cited

U.S. PATENT DOCUMENTS

| | | | |
|---|---|---|---|
| 3,598,122 | 8/1971 | Zaffaroni | 128/268 |
| 3,989,816 | 11/1976 | Rajadhyaksha | 424/60 |
| 4,060,084 | 11/1977 | Chandrasekaran et al. | 128/260 |
| 4,316,893 | 2/1982 | Rajahyaksha | 424/180 |
| 4,379,454 | 4/1983 | Campbell et al. | 604/897 |
| 4,405,616 | 9/1983 | Rajahyaksha | 424/244 |
| 4,650,484 | 3/1987 | Shaw et al. | 128/268 |
| 4,695,277 | 9/1987 | Lauk | 604/304 |
| 4,710,191 | 12/1987 | Kwiatek et al. | 604/897 |
| 4,849,224 | 7/1989 | Chang et al. | 424/434 |
| 4,863,970 | 9/1989 | Patel et al. | 514/784 |
| 4,983,395 | 1/1991 | Chang et al. | 424/448 |

FOREIGN PATENT DOCUMENTS

| | | |
|---|---|---|
| 0040861 | 12/1981 | European Pat. Off. . |
| WO 92/10154 | 6/1992 | WIPO . |
| WO 9323019 | 11/1993 | WIPO . |

OTHER PUBLICATIONS

Idson et al., "Precutaneous absorption" *J. Pharm. Sci.* (1975) 64:901–924.

*Primary Examiner*—James J. Seidleck
*Assistant Examiner*—Michael A. Williamson
*Attorney, Agent, or Firm*—Morrison & Foerster LLP

[57] ABSTRACT

A device for administering an active agent to the skin or mucosa of an individual comprising a laminated composite of an adhesive overlay, a backing layer underlying the central portion of the adhesive overlay, an active agent-permeable membrane, the backing layer and membrane defining a reservoir that contains a formulation of the active agent, a peel seal disc underlying the active agent-permeable membrane, a heat seal about the periphery of the peel seal disc, the active agent-permeable membrane and the backing layer and a removable release liner underlying the exposed overlay and peel seal disc. The adhesive layer is above and peripheral to the path of the active agent to the skin or mucosa and is protected from degradation by the components of the reservoir by a multiplicity of heat seals. The peel seal disc protects against release of the active agent-containing reservoir and the release liner protects the adhesive from exposure to the environment prior to use.

20 Claims, 4 Drawing Sheets

TRANSDERMAL DELIVERY SYSTEM WITH ADHESIVE OVERLAY AND PEEL SEAL DISC

This application is a continuation of U.S. Ser. No. 08/361,800, filed Dec. 21, 1994, now abandoned, the contents of which are hereby incorporated by reference into the present disclosure.

TECHNICAL FIELD

This invention is in the field of transdermal and transmucosal administration of active agents (drugs). More particularly, it relates to a device for achieving such administration that has an active agent-containing reservoir and an adhesive layer for affixing the device to the skin or mucosa. The adhesive layer is above and peripheral to the path of the active agent to the skin or mucosa and is protected from degradation by the components of the reservoir by a multiplicity of heat seals. A peel seal disc protects against release of the active agent-containing reservoir and a release liner protects the adhesive from exposure to the environment prior to use.

BACKGROUND OF THE INVENTION

Devices for administering drugs through the skin or mucosa have been described in many patents. These devices are usually of two types: matrix systems and liquid reservoir systems. Both systems are laminated composites that have, from basal to top, a peelable release liner, a pressure sensitive adhesive layer for attaching the device to the skin, a drug-containing layer, and a drug impermeable backing layer. In the matrix type system, the drug is dispersed within a solid or semi-solid carrier. In the reservoir type system, the drug, typically in liquid solution, is contained within a walled container, usually formed between the backing layer and a drug-permeable membrane layer.

A number of reservoir type systems have been described. U.S. Pat. No. 4,710,191 to Kwiatek et al. involves a reservoir type device that includes a peelable heat sealed release liner layer underlying the reservoir and the portion of the backing layer that extends beyond the reservoir. In a second embodiment, a microporous membrane is included between the backing layer and the reservoir.

U.S. Pat. No. 4,829,224 to Chang et al. describes a device with a reservoir that is defined by a backing layer and a drug-permeable membrane layer. A ring-shaped layer made of an adhesive is peripheral to the reservoir. A peelable liner layer underlies the membrane. A second peelable layer, the release liner, underlies the entire assembly. A first heat seal connects the backing layer and the membrane and surrounds the reservoir. A second heat seal concentric about the first heat seal connects the backing layer and the release liner. The second heat seal is broken when the release liner is removed. The device may include an inner liner that underlies the membrane and portions of the backing layer. This inner liner is removed following removal of the release liner so that the membrane is exposed.

U.S. Pat. No. 4,983,395 to Chang et al. relates to another device with a backing layer and a membrane layer that define a reservoir. A peelable inner liner underlies the reservoir and portions of the backing and membrane layers outside the periphery of the reservoir. An adhesive layer underlies the inner liner and remaining portions of the backing and membrane layers. A peelable release liner underlies the adhesive layer. A first heat seal connects the backing and membrane layers on the periphery of the reservoir. A second heat seal underlies the first heat seal and connects the membrane and the inner liner. In use, the release liner and inner liner are peeled away to expose the undersurfaces of the membrane and adhesive layers prior to placement of the device onto the skin or mucosa.

The present invention is an improved device for transdermal or transmucosal drug delivery in which an occlusive peel seal layer underlies the drug containing reservoir and serves to prevent release of the drug prior to use. A release liner overlays the peel seal layer and exposed portions of the adhesive overlay. In this way, the release liner need not be occlusive and thus may be chosen from a wide variety of materials that can be breathable, and can have a stretchable, elastic quality. Such devices are cost efficient and easy to manufacture.

In addition, in the devices of this invention only the central portion of the device in line with the reservoir is occlusive, leaving the portion of the device peripheral to the central portion nonocclusive or breathable.

DISCLOSURE OF THE INVENTION

The invention is a device for administering an active agent to the skin or mucosa of an individual comprising a laminated composite of:

(a) an adhesive overlay having a central portion and a peripheral portion;

(b) a backing layer underlying the central portion of the adhesive overlay;

(c) an active agent-permeable membrane underlying the backing layer, the backing layer and membrane defining (d) a reservoir therebetween that contains an active agent;

(e) a peel seal disc underlying the active agent-permeable membrane;

(f) a heat seal about the periphery of the peel seal disc, the active agent-permeable membrane and the backing layer; and (g) a removable release liner underlying the peripheral portion of the adhesive overlay and the peel seal disc.

MODES FOR CARRYING OUT THE INVENTION

Figure 1:
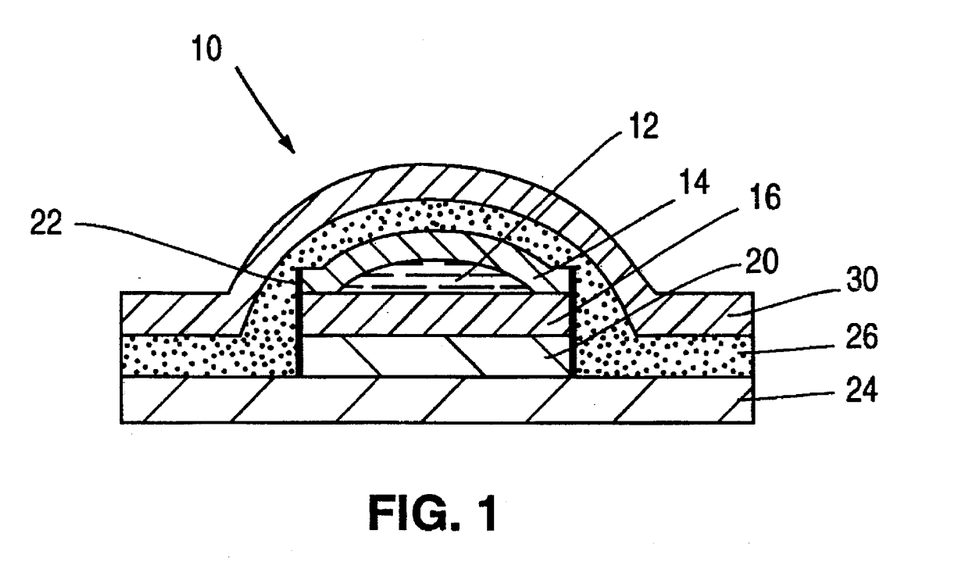
FIG. 1 is an enlarged sectional view of one embodiment of the device of the invention.

FIG. 1 shows a device, generally designated 10 that is designed to administer a formulation of an active agent to the skin or mucosa. The device 10 is a laminated composite. A drug reservoir 12 is formed between an upper backing layer 14 and an underlying drug-permeable membrane layer 16. A peel seal disc 20 is placed beneath the membrane layer 16. The three layers, the backing layer 14, the membrane layer 16 and the peel seal disc 20 are heat sealed together at their periphery 22, the membrane layer 16 being heat sealed to the backing layer 14 and the peel seal disc 20 being heat sealed to the membrane layer 16. A release liner 24 is placed underneath the peel seal disc 20 and extends beyond the peripheral heat seal 22. An adhesive layer 26 overlies the backing layer 14 and the portions of the release liner 24 that extend beyond the peripheral heat seal 22. An uppermost overlay layer 30 overlies the adhesive layer 26. In this embodiment the release liner is removed together with the peel seal disc prior to placing the device on the skin.

Figure 2A:
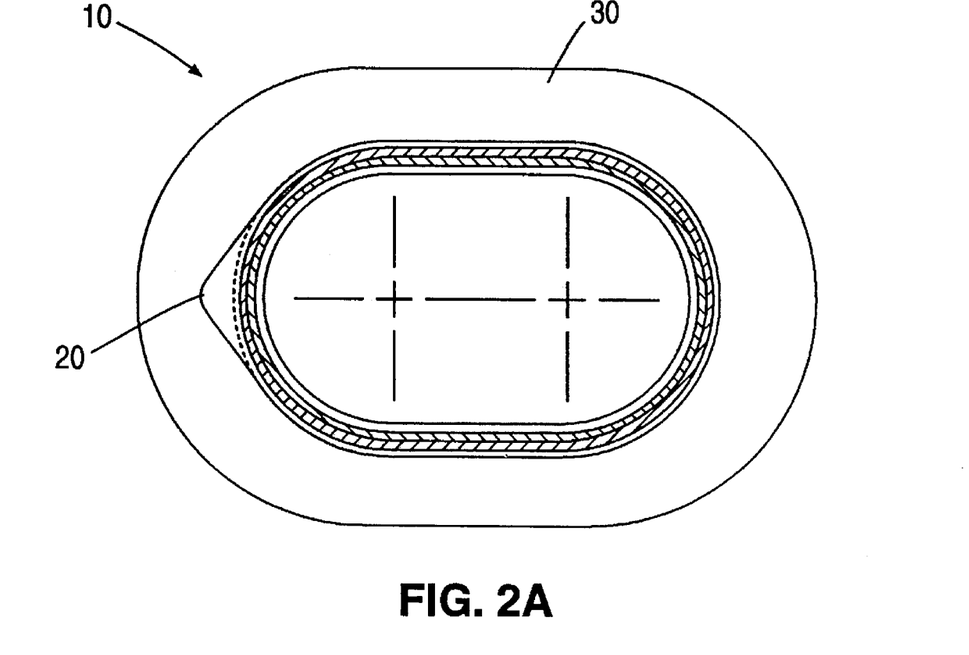
FIGS. 2A and 2B are enlarged top views of further embodiments of the device of the invention.
Figure 2B:
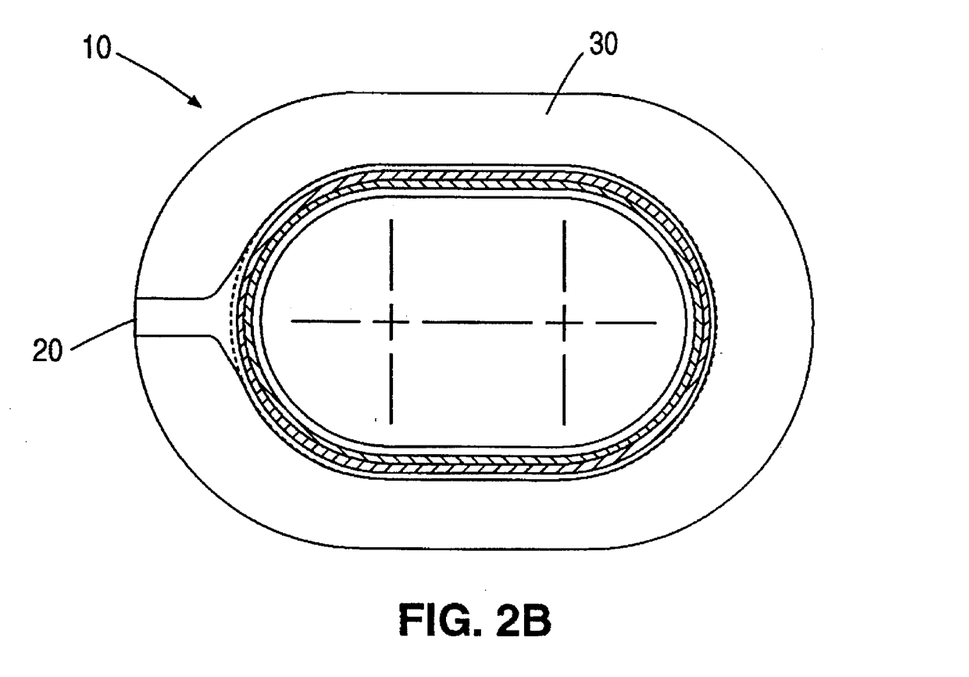

FIGS. 2A and 2B show further embodiments of the device where a tab 32 extends past the heat seal 22 and allows for easy removal of the peel seal disc 20. The tab 32 may extend a short distance past the heat seal 22 as shown in FIG. 2A or may extend to the periphery 34 of the device 10 as shown in FIG. 2B.

Figure 3:
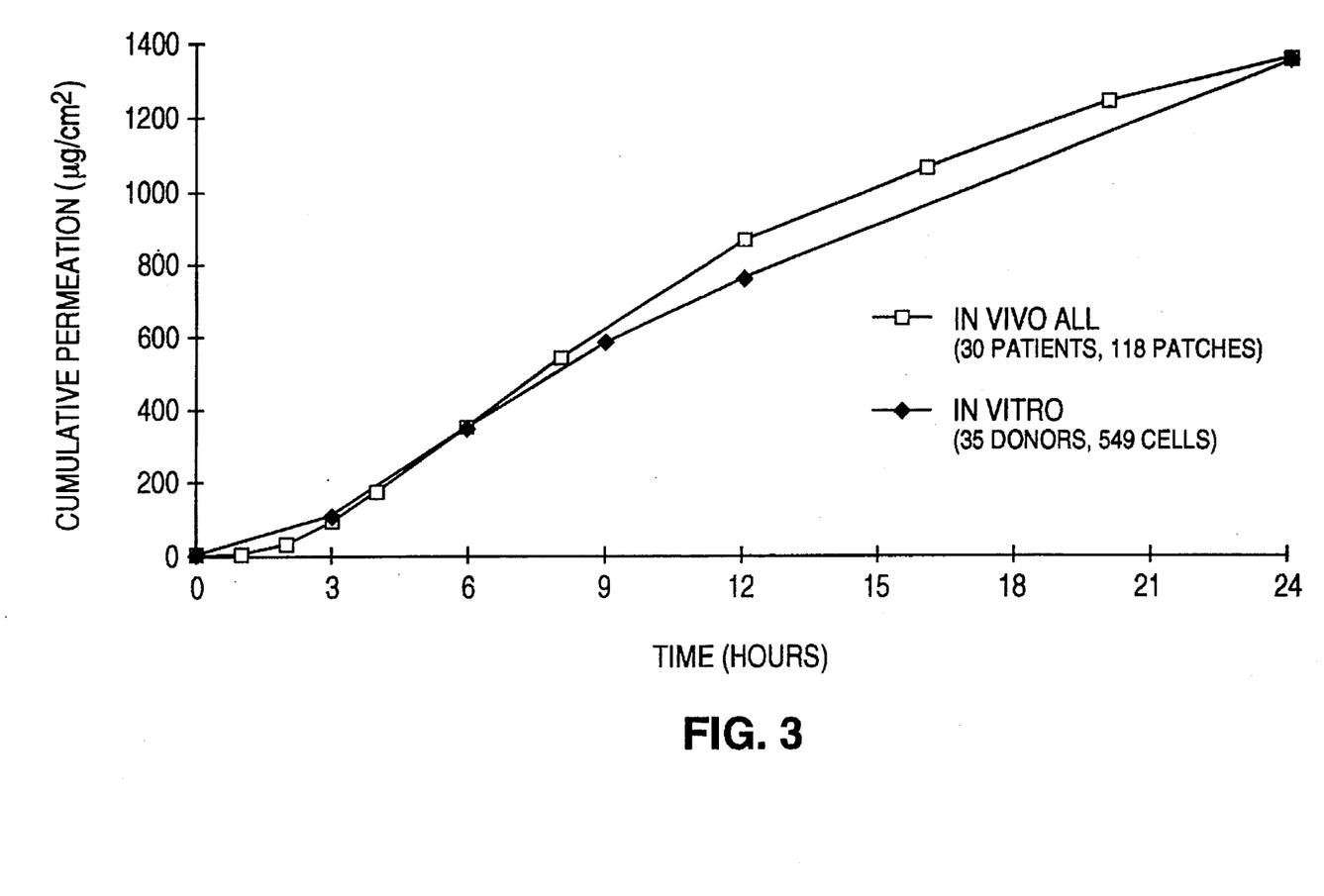
FIG. 3 is an enlarged sectional view of another embodiment of the invention.
Figure 4:
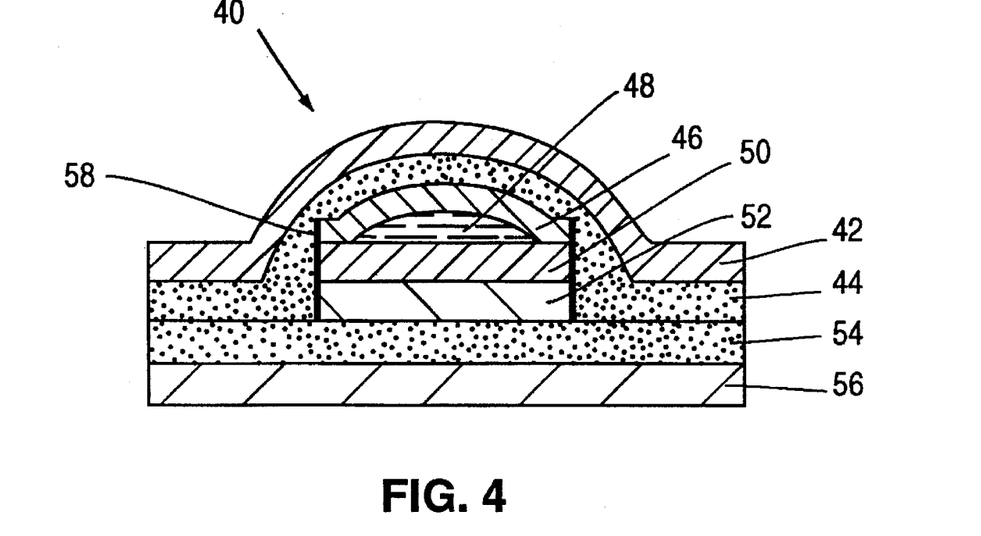
FIG. 4 is an enlarged view of the embodiment of FIG. 3 showing the embodiment disassembled.

FIGS. 3 and 4 depict another embodiment, generally designated 40, of the laminated composite of the invention. The device of FIGS. 3 and 4 differs from that of FIG. 1 by the presence of a second adhesive layer that underlies the peel seal disc and the peripheral portion of the first adhesive layer. More specifically, device 40 consists of (from top surface to basal surface) a nonocclusive overlay layer 42, a first adhesive layer 44, a backing layer 46, a drug reservoir 48 comprising a solution or gelled formulation of a transdermally administrable drug; a drug-permeable membrane layer 50; a peel seal disc 52, a second adhesive layer 54, and a release liner layer 56. As shown, the backing film, reservoir, membrane, and peel seal disc are "in-line" and have smaller areas than the overlay, the two adhesive layers and the release liner. The latter extend peripherally beyond the entire periphery of the former. The backing film, membrane, and peel seal disc are heat sealed at 60 about their entire peripheries.

In use the release liner layer, the portion of the second adhesive layer that underlies the peel seal disc, and the peel seal disc are separated from the rest of the assembly. The separated or disassembled configuration is shown in FIG. 4. In this regard, the relative bond strengths between the release layer and the second adhesive layer, the second adhesive layer and the first adhesive layer and peel seal disc, and the peel seal disc and membrane are such that when the release liner is removed, the central portion of the second adhesive layer and the peel seal disc are removed with it. The removed release layer subassembly is discarded. The subassembly containing the drug reservoir is placed on the skin, with the peripheral ring of the second adhesive layer being the means by which that subassembly is affixed to the skin or mucosa. When so placed on the skin the drug reservoir is in diffusional communication with the skin via the membrane. In other words, drug is free to diffuse through the membrane to the skin.

The backing layer 14 or 46 of the device may be composed of a single film or a plurality of films. In any event, its inner surface must be capable of being heat sealed to the membrane layer 16 or 50. One or more of the films that constitute the backing layer will be impermeable to components of the drug formulation contained in the reservoir. Examples of materials used as backing layers in transdermal delivery devices that may find use in the present invention are polyethylene, polypropylene, polyvinylchloride, polyethylene terephthalate, ethylene-vinyl acetate copolymers and combinations thereof. The layer may include one or more metal layers and/or one or more fibrous layers. Preferably the backing layer is occlusive.

The term "active agent" or "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the inventive device are antiinflammatory drugs, analgesics, antiarthritic drugs, antispasmodics, antidepressants, antipsychotic drugs, tranquilizers, antianxiety drugs, narcotic antagonists, antiparkinsonism agents, cholinergic agonists, anticancer drugs, immunosuppression agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents, cardiovascular drugs, and the like. The appropriate drugs of such types are capable of permeating through the skin either inherently or by virtue of treatment of the skin with a percutaneous absorption enhancer. Because the size of the device is limited for patient acceptance reasons, the preferred drugs are those that are effective at low concentration in the blood stream. Examples of specific drugs are steroids such as estradiol, progesterone, norgestrel, levonorgestrel, norethindrone, medroxyprogesterone acetate, 3-ketodesogestrel, testosterone and their esters, nitro-compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, naloxone, codeine, dihydroergotamine, pizotiline, salbutamol, terbutaline, prostaglandins such as misoprostol and enprostil, omeprazole, imipramine, benzamides such as metoclopamine, scopolamine, peptides such as growth releasing factor and somatostatin, clonidine, dihydropyridines such as nifedipine, verapamil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions and the salts of such compounds with pharmaceutically acceptable acids or bases.

In addition to the drugs described above, depending on the permeability of the skin to the drug or drugs, the reservoir may also contain a percutaneous absorption enhancer that increases the permeability of the skin to the drug or drugs and is coadministered to the skin. Examples of percutaneous absorption enhancers are those referred to in U.S. Pat. Nos. 3,989,816, 4,863,970, 4,316,893, 4,405,616, 4,060,084 and 4,379,454 and *J. Pharm Sci* (1975) 64:901–924. The formulation contained in the reservoir may further include solvents, gelling agents, stabilizers, antiirritants, and other additives.

The membrane layer 16 or 50 is permeable to the drug. It may be a "dense" membrane made of material that is inherently permeable to the components of the reservoir that are to be administered to the skin or mucosa or it may be made of a microporous membrane whose pores are filled with a drug-permeable material including the drug reservoir formulation itself which may include enhancers where desired. In the case of dense membranes, the components dissolve in the material and diffuse through the material to the skin. In the case of microporous materials, the components diffuse through the pores to the skin. The membrane may or may not be a rate-controlling element depending upon the particular drug involved, the permeability of the skin to the drug, and the rate of delivery required to provide therapy. Examples of materials for making dense membranes are given in U.S. Pat. Nos. 3,598,122 and 4,650,484. Examples of materials for making microporous membranes are provided in U.S. Pat. Nos. 3,797,494 and 4,031,8943.

The adhesive layers 26, 44 and 54 are composed of pressure sensitive surgical adhesive such as those that are commonly used to affix transdermal drug delivery devices, bandages or other dressings to the skin. Examples of such adhesives are polyisobutene (PIB), natural rubber adhesives, acrylate and methacrylate adhesives and silicone adhesives. Breathable, nonocclusive adhesives such as the acrylate/methacrylate and silicone adhesives are preferred.

The peel seal disc 20 or 52 may be composed of a single layer or a multiplicity of layers. The disc should be (1) impermeable to the components of the drug reservoir formulation that diffuse through the membrane, (2) heat-sealable to the membrane layer, and (3) inherently strippable or rendered so by techniques such as silicone or fluorocarbon treatment or surface treatment with a seal incompatible layer. Suitable peel seal discs include those made from Bertek 4418 Peelable Seal, Total Healthcare Packaging TPC-0812 or TPC-0760 and UCB Medical Industries LR 4/25.

The release liner 24 or 56 may similarly be composed of a single layer or a multiplicity of layers. Unlike the peel seal disc, however, the release liner need not be impermeable to the components of the drug formulation in that the peel seal disc protects against release of the components from the reservoir. Therefore, suitable release liners may be made from materials such as polyester, low density polyethylene (LDPE), high density polyethylene (HDPE), polypropylene, polystyrene, polyamide, nylon, polyvinyl chloride and specialty papers, and include Akrosil Biorelease liners, Scotchpak 1022 release liners, Adhesives Research AR5MS, Custom Coating and Laminating 7000 on HDPE or 6020 on polyethylene terephthalase (PET).

The overlay layer 30 or 42 overlies the adhesive layer 26 or 44 and may be made from materials such as polyolefin, polyurethane, nylon, polyester, vinyl, acetate taffeta or other elastomeric woven or nonwoven fabrics or films. Preferably the overlay material is nonocclusive (breathable).

The respective components of the device may be formulated and assembled using procedures that are known in the drug formulation, transdermal device and laminating arts. The shape of the device is not critical, and devices of preformed shapes may be assembled directly or punched, cut or otherwise formed from large sheets of laminated composite.

The following examples further illustrate the invention. These examples are not intended to limit the invention in any manner.

EXAMPLES

Example 1

A medical grade, pressure sensitive acrylic adhesive, MA-31 (Adhesives Research, Glen Rock, Pa.) was coated onto a low peel strength, siliconized release liner using a 10 mil gap casting knife. The adhesive solvent was evaporated at 80° C. for 15 min. to provide a final dry adhesive thickness of 0.002 inches. Volara Foam 15EO (Voltek, Division of Sekisui America Corp, Lawrence, Mass.) the overlay material, was then laminated onto the dry adhesive film forming the overlay adhesive laminate. This overlay adhesive laminate was used at a later stage of the fabrication process as described below.

A gelled testosterone formulation was prepared by dissolving 15 mg/ml testosterone in a solution containing 50.0/15.0/30.0/2.5/2.5% (v/v) of ethanol/water/glycerin/glycerol monooleate/methyl laureate. The resulting solution was gelled with 3.0% (w/v) of Carbopol 1342. The pH of the resulting gel was adjusted to 4.5 to 5.0 by addition of 2N sodium hydroxide.

The overlay patch with peel seal disc was fabricated as follows: A CoTran 9711 microporous membrane (3M, St. Paul, Minn.) was placed over an LR4/25 peel seal disc film (UCB Medical Industries, Bloomfield, Conn.). 0.9 g of the testosterone formulation was dispensed onto the microporous membrane. The backing film (Scotchpak 1012, 3M, St. Paul Minn.) was predimpled to provide a flat, circular cup with a volume of approximately 1.0 cc. This predimpled backing film was placed over the gel such that the dimple in the backing film was centered on the mound of gel. The backing film was then heat sealed to the microporous membrane/peel seal film laminate at 370° F. with a pressure of 30 psi and a 0.4 sec. dwell time. A circular heat seal die with a interior diameter of 1.22 inches and a heat seal width of 0.03 inch was used. A gel containing reservoir with an active surface of 7.5 $cm^2$ was formed. This heat sealing step simultaneously creates a permanent reservoir seal between the microporous membrane and the backing film and a peelable seal between the microporous membrane and the peel seal disc film. This intermediate drug containing reservoir system, with a diameter of 3.5 cm and a total surface area of 9.6 $cm^2$, was then diecut from the heat sealed laminate.

The above reservoir system was laminated to the previously prepared overlay adhesive laminate by removing the protective release liner from the overlay adhesive, placing the diecut reservoir system onto the adhesive with the backing film contacting the adhesive, relaminating the release liner over the exposed adhesive and finally diecutting the actual overlay adhesive transdermal delivery system from this laminate. The cutting die used for this operation has a diameter of 5.5 cm thereby diecutting a transdermal delivery system with a final surface area of 23.8 $cm^2$, which includes the peripheral adhesive area. The activation of this system before application to the skin proceeds in a two step process: the release liner covering the adhesive is removed first, followed by the removal of the peelable disc film protecting the reservoir.

Example 2

Transdermal systems with an adhesive overlay were made using the procedure described in Example 1, except that the adhesive used was a medical grade acrylic adhesive, Gelva 737 (Monsanto, St. Louis, Mo.).

Example 3

Transdermal systems with an adhesive overlay were made using the procedure described in Example 1, except that the adhesive used was a medical grade PIB adhesive MA-24 (Adhesives Research, Glen Rock, Pa.).

Example 4

Transdermal systems with an adhesive overlay were made using the procedure described in Example 1, except that a silicone based adhesive, BIO PSA X7-2920 (Dow Corning, Midland, Mich.) was used. The release liner used was the Akrosil BioRelease liner (Menasha, Wis.) which is compatible with the above silicone adhesive.

Example 5

Transdermal systems with an adhesive overlay were made using the procedure described in Example 1, except that the adhesive used was an (acrylic copolymer) adhesive, TSR Adhesive (Sekisui Chemical Company, Osaka, Japan).

Example 6

Transdermal systems with an adhesive overlay were made using the same procedure as described in Example 1, except that the peel seal disc film was a multilaminate PET/LDPE/Foil/Primacor 3440/LLDPE/Heat Seal Film flexible packaging material, TPC-0812 (Tolas Healthcare Packaging, Feasterville, Pa.).

Example 7

Transdermal systems with an adhesive overlay were made using the same procedure as described in Example 1, except that the peel seal disc film was a Peelable Foil Film material, a multilaminate of PET/adhesive/Foil/adhesive/LLDPE/Heat Seal Film (Technipaq, Crystal Lake, Ill.).

Example 8

Transdermal systems with an adhesive overlay were made using the procedure described in Example 1, except that the overlay material was an embossed polyurethane elastomeric film.

Example 9

Transdermal systems with an adhesive overlay were made using the procedure described in Example 1, except that the overlay material was a 100% nonwoven polyester fabric.

Example 10

Transdermal systems with an adhesive overlay were made using the procedure described in Example 1, except that the overlay material was a spunbonded nylon film.

Example 11

Transdermal systems with an adhesive overlay were made using the procedure described in Example 1, except that the overlay material was a woven acetate taffeta film.

Example 12

A 4 in.×4 in. commercially available wound dressing, Mitraflex® Plus, distributed by Calgon Vestal Laboratories, was used as the adhesive overlay.

A gelled ketorolac tromethamine formulation was prepared by dissolving 60 mg/ml ketorolac tromethamine in a solution containing 55.28/33.17/10.0/1.55% (v/v) of isopropyl alcohol/water/glycerin/isopropyl myristate. The resulting solution was gelled with 5.0% w/v) of Natrosol® Plus 330 CS and the pH of the resulting gel was adjusted to 5.1±(0.2) by addition of 2N HCl. The gel also contained 0.1% (w/v) butylated hydroxy toluene as an antioxidant.

The overlay patch with peel seal disc was fabricated as follows: A CoTran 9710 microporous membrane was placed over an LR4/25 peel seal disc film. 3.44 g of the ketorolac tromethamine formulation was dispensed onto the microporous membrane. The backing film was predimpled to provide a flat, circular cup. This predimpled backing film was placed over the gel such that the dimple in the backing film was centered on the mound of gel. The backing film was then heat sealed to the microporous membrane/peel seal film laminate at 370° F. with a pressure of 30 psi and a 0.4 sec. dwell time. An oval heat seal die was used to form a gel containing reservoir with an active surface of 30 cm². This heat sealing step simultaneously creates a permanent reservoir seal between the microporous membrane and the backing film and a peelable seal between the microporous membrane and the peel seal disc film. This intermediate drug containing reservoir system, with a total surface area of 42.55 cm², was then diecut from the heat sealed laminate.

The above reservoir systems were laminated to the Mitraflex® Plus overlay adhesive laminate by removing the protective release liner from the wound dressing, placing the diecut reservoir system onto the adhesive with the backing film contacting the adhesive and relaminating the release liner over the exposed adhesive to obtain the actual overlay adhesive transdermal delivery system. The activation of this system before application to the skin proceeds in a two step process: the release liner covering the adhesive is removed first, followed by the removal of the peelable disc film protecting the reservoir.

Example 13

Transdermal systems with an adhesive overlay were made using the procedure described in Example 12, except that the overlay adhesive laminate used was fabricated as in Example 1. The final surface area of the transdermal delivery system was 63 cm².

Example 14

Transdermal systems with an adhesive overlay were made using the procedure described in Example 13, except that the adhesive used was a medical grade PIB adhesive, MA-24 (Adhesives Research, Glen Rock, Pa.).

Example 15

Transdermal systems with an adhesive overlay were made using the procedure described in Example 13, except that a silicone based adhesive, BIO PSA X7-2920 (Dow Corning, Midland, Mich.). The release liner used was the Akrosil BioRelease liner (Menasha, Wis.) which is compatible with the above silicone adhesive.

Example 16

Transdermal systems with an adhesive overlay were made using the procedure described in Example 13, except that the adhesive used was an acrylic copolymer adhesive, TSR Adhesive (Sekisui Chemical Company, Osaka, Japan.

Example 17

Transdermal systems with an adhesive overlay were made using the procedure described in Example 13, except that the peel seal disc film was a multilaminate of PET/LDPE/Foil/Primacor 3440/LLDPE/Heat Seal film flexible packaging material, TPC-0812 (Tolas Healthcare Packaging, Feasterville, Pa.).

Example 18

Transdermal systems with an adhesive overlay were made using the same procedure as described in Example 13, except that the peel seal disc film was a Peelable Foil Film, a multilaminate PET/adhesive/Foil/adhesive/LLDPE/Heat Seal Film (Technipaq, Crystal Lake, Ill.).

Example 19

Transdermal systems with an adhesive overlay were made using the procedure described in Example 13, except that the overlay material was an embossed polyurethane elastomeric film.

Example 20

Transdermal systems with an adhesive overlay were made using the procedure described in Example 13, except that the overlay material was a 100% nonwoven polyester fabric.

Example 21

Transdermal systems with an adhesive overlay were intermediate drug-c made using the procedure described in Example 13, except that the overlay material was a spun-bonded nylon film.

Example 22

Transdermal systems with an adhesive overlay were made using the procedure described in Example 13, except that the overlay material was a woven acetate taffeta film.

Example 23

Ketorolac tromethamine gel composition was prepared as described in Example 12. The gel was evaluated for in vitro skin flux performance.

In vitro human cadaver skin flux studies were conducted using modified Franz diffusion cells, placed in a water bath calibrated to maintain the skin surface temperature at 32° C. The epidermal membrane was separated from the full thickness human cadaver skin by the method of Kligman and Christopher (Arch. Dermatol. 88, 702–705, 1963). The full thickness skin was exposed to 60° C. heat for 60 seconds. The stratum corneum and epidermis were gently peeled from the dermis. The epidermal membrane was mounted onto a 0.65 cm$^2$ surface area diffusion cell with the epidermal side facing the receiver compartment and clamped in place. The receiver compartment was then filled with an aqueous solution containing 0.02% sodium azide as a bacteriostat. The cell was placed in a circulating water bath calibrated to maintain skin surface temperature at 32°±1° C. and the skin was allowed to hydrate overnight. The subsequent morning, 75 µl of the gelled ketorolac formulation was pipetted into a cavity created by placing a Teflon washer over the stratum corneum surface. The cavity was then occluded by clamping an occlusive backing film over the Teflon washer assembly. Throughout the experiment, the receiver compartment, which contained a bar magnet, was continuously stirred by a magnetic stirrer placed under the water bath. At predetermined intervals, the entire contents of the receiver compartment was collected for drug quantitation using the HPLC method in Table I. The receiver compartment was refilled with fresh receptor medium, taking care to eliminate any air bubbles at the skin/solution interface. From the concentration versus time curve, the average steady state flux, the interval flux and cumulative delivery per unit area at 24 hours were calculated. The in vivo delivery was projected by multiplying the in vitro cumulative delivery (µg/cm$^2$/24 h) by the patch active area (30 cm$^2$).

TABLE I

| In Vitro Skin Flux HPLC Method | |
| --- | --- |
| Column: | Partisphere C-18 (100 mm) |
| Flow Rate: | 1.0 ml/min |
| Wavelength: | 314 nm |
| Injection Volume: | 10 µl |
| Retention Time: | 2.0 ± 0.3 min |
| Mobile Phase: | 60/40/0.5 (% v/v) Acetonitrile/H$_2$O/Glacial Acetic Acid pH ~ 3.0 |

Overlay patches, prepared as described in Example 12, were applied to the chest in 24 healthy adult volunteers (12 male and 12 female) in human clinical trials. Plasma samples were collected for ketorolac quentitation at predetermined times. After removal of the patches in each study, the used patches were extracted in 100 ml of methanol and analyzed for drug content using the HPLC method described in Table II. The difference between the initial and final patch drug contents gave the amount of ketorolac delivered, based on patch depletion analysis.

TABLE II

| Patch Content Assay HPLC Method | |
| --- | --- |
| Column: | Zorbax RX-C8 5 µm, 15 cm × 4.6 mm |
| Flow Rate: | 1.0 ml/min |
| Wavelength: | 314 nm |
| Injection Volume: | 10 µl |
| Retention Time: | 5.2 ± 0.2 min |
| Mobile Phase: | 60/40/1 (% v/v) Acetonitrile/H$_2$O/Glacial Acetic Acid pH ~ 3.0 |

Figure 5:
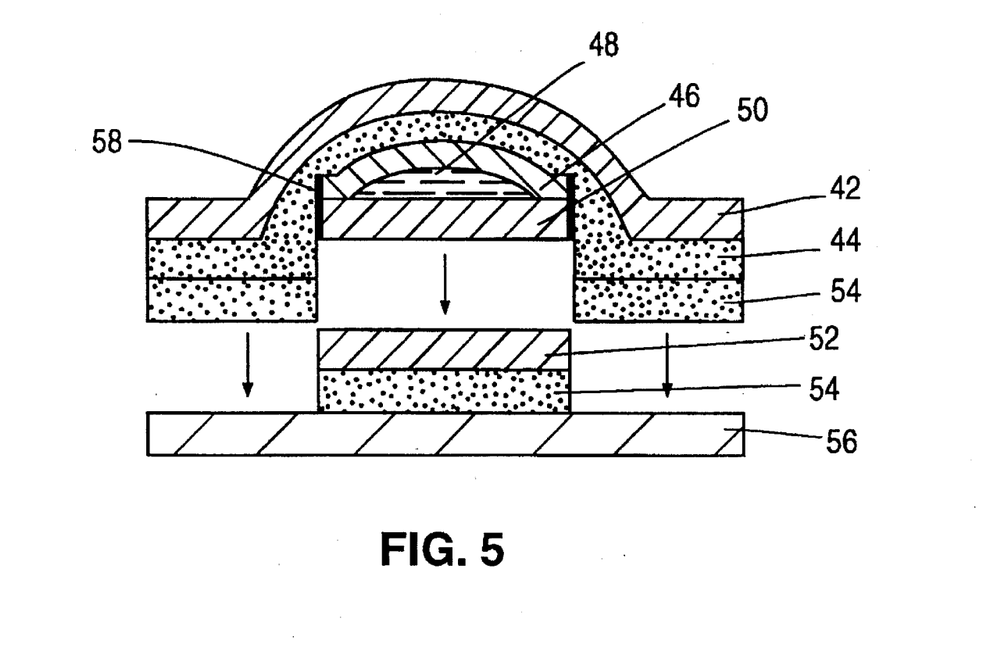
FIG. 5 is a graph showing a comparison of calculated and experimental cumulative release kinetics of keterolac tromethamine based on the tests described in Example 23.

Table III compares the in vivo cumulative delivery, based on patch depletion analysis, with the projected drug delivery for the 30 cm$^2$ overlay patch, based on in vitro skin flux results. The projected drug delivery is based upon average in vitro cumulative deliver (µg/cm$^2$/24 h) multiplied by the active area (30 cm$^2$) of the overlay patch. The average in vivo dose was calculated from the difference between initial drug content of the patches and the residual drug content of the patches upon removal. In vivo, the 30 cm$^2$ overlay patch delivered (46.4±17.5) mg/day of ketorolac tromethamine, in very good agreement with the predicted value of 53.7 mg/day. FIG. 5 shows that the average in vivo cumulative input kinetics, calculated according to the method of Wagner and Nelson (J. Pham. Sci. 52, 610–611, 1963) is in very good agreement with the in vitro cumulative input kinetics.

TABLE III

| Projected and observed In Vivo Performance of overlay Patch System | | |
| --- | --- | --- |
| Patch System | Projected Dose Ketorolac Tromethamine (mg/day) | In Vivo Dose Ketorolac Tromethamine (mg/day) |
| 30 cm$^2$ Overlay Patch | 53.7 | 46.4 ± 17.5 (24 subjects) |

Example 24

Transdermal systems with an adhesive overlay were made using the procedure described in Example 1, except that the die used to diecut the liquid reservoir portion of the transdermal delivery system allowed the peel seal disc tab to reach the edge of the release liner, as shown in FIG. 2B. This extended tab allows the final system to be activated in a single step process, instead of the two step process described in Example 1. In the single step process, the release liner and the extended tab of the peel seal disc are held between the thumb and index finger of one hand and the backing film in the other. The peel seal disc and release liner are pulled apart from the backing film to activate the system.

Example 25

A medical grade pressure sensitive adhesive, MA-31 (Adhesives Research, Glen Rock, Pa.) was coated onto a high peel strength, siliconized release liner using a 10 mil gap casting knife. The adhesive solvent was evaporated at 80° C. for 15 min. to provide a final dry adhesive thickness of 0.0015 inches. A low strength, in-process, 2 mil high density polyethylene siliconized liner was then laminated onto the dry adhesive film forming the primary adhesive laminate. This primary adhesive laminate, and the overlay adhesive laminate fabricated as described in Example 1, were used at a later stage of the fabrication process as described below.

The intermediate drug containing reservoir was fabricated as an Example 1, except that the weight of the testosterone gel was 1.8 g, the active surface was 15 cm², and the total surface area was 18.4 cm². This reservoir system was laminated to the primary adhesive laminate by removing the in-process liner, placing the diecut reservoir centrally onto the adhesive with the peel-seal disc film contacting the adhesive. The protective liner from the overlay adhesive laminate was then removed and the overlay adhesive laminated onto the primary adhesive/reservoir system, such that the overlay adhesive was in contact with the backing film of the intermediate drug-containing reservoir and also the adhesive area of the primary adhesive laminate extending beyond the intermediate drug-containing reservoir. The final overlay adhesive transdermal delivery system was diecut from this laminate structure to give a system with a total surface area of 33 cm².

The activation of this system is carried out in a single step by pulling away the high peel strength liner from the overlay adhesive. The peel-seal disc remains anchored to the liner, thereby exposing the reservoir area.

Example 26

Transdermal systems with an adhesive overlay were made using the same procedure as described in Example 25, except that the adhesive used in the primary adhesive laminate and the overlay adhesive laminate was a medical grade polyisobutene (PIB) adhesive MA-24 (Adhesives Research, Glen Rock, Pa.).

Example 27

Transdermal systems with an adhesive overlay were made using the same procedure as described in Example 25, except that the adhesive used in the primary adhesive laminate and the overlay adhesive laminate was a silicone based adhesive, BIO PSA X7-2920 (Dow Corning, Midland, Mich.).

Modifications of the above-described modes for carrying out the invention that are obvious to those of skill in the fields of chemistry, transdermal drug delivery, pharmacology and related fields are intended to be within the scope of the following claims.

We claim:

1. A device for administering an active agent to the skin or mucosa of an individual comprising a laminated composite of:
   (a) a backing layer defining an upper portion of a reservoir and extending to the periphery of a peel seal disk;
   (b) an active agent-permeable membrane extending to the periphery of the peel seal disk and the backing layer, and underlying the backing layer, the backing layer and membrane defining
   (c) the reservoir therebetween that contains a formulation of the active agent;
   (d) the peel seal disc underlying an active agent-permeable membrane;
   (e) a heat seal about the periphery of the peel seal disc, the active agent-permeable membrane and the backing layer;
   (f) an adhesive overlay having a central portion overlying the backing layer and a peripheral portion that extends beyond the periphery of the peel seal disc; and
   (g) a removable release liner underlying the peripheral portion of the adhesive overlay and the peel seal disc.

2. The device of claim 1 wherein the adhesive is made of a material selected from the group consisting of polyisobutenes, natural rubbers, acrylates, methacrylates and silicone.

3. The device of claim 1 wherein the backing layer comprises at least one impermeable film layer.

4. The device of claim 1 wherein the membrane is selected from the group consisting of microporous membranes and dense membranes.

5. The device of claim 1 wherein the peel seal disc is composed of at least one layer.

6. The device of claim 1 further comprising a percutaneous absorption enhancer.

7. The device of claim 1 wherein the formulation further comprises a material selected from the group consisting of a solvent, a gelling agent, stabilizer and an anti-irritant.

8. The device of claim 1 including an adhesive layer that underlies the peripheral portion of the adhesive overlay and the peel seal disc and overlies the release liner.

9. The device of claim 1 wherein the adhesive overlay is nonocclusive and the backing layer is occlusive.

10. A device for administering an active agent to the skin or mucosa of an individual comprising a laminated composite of:
   (a) a backing layer defining an upper portion of a reservoir and extending to the periphery of a peel seal disc;
   (b) an active agent-permeable membrane extending to the periphery of the peel seal disc and the backing layer, and underlying the backing layer, the backing layer and the membrane defining
   (c) the reservoir therebetween that contains a formulation of an active agent;
   (d) the peel seal disc underlying the active agent-permeable membrane;
   (e) a heat seal about the periphery of the peel seal disc, active agent-permeable membrane and backing layer;
   (f) an adhesive overlay having a central portion overlying the backing layer and a peripheral portion that extends beyond the peripheral of the peel seal disc;
   (g) a removable release liner underlying the peripheral portion of the adhesive overlay and the peel seal disc and extending beyond the peripheral portion; and
   (h) a second adhesive layer underlying the peelable disk and peripheral region of the adhesive overlay, the second adhesive layer extending beyond the periphery of the backing film, the reservoir, and the membrane.

11. The device of claim 10 wherein the adhesive is made of a material selected from the group consisting of polyisobutenes, natural rubbers, acrylates, methacrylates and silicone.

12. The device of claim 10 wherein the backing layer comprises at least one impermeable film layer.

13. The device of claim 10 wherein the membrane is selected from the group consisting of microporous membranes and dense membranes.

14. The device of claim 10 wherein the peel seal disc is composed of at least one layer.

15. The device of claim 10 further comprising a percutaneous absorption enhancer.

16. The device of claim 10 whenever the formulation further comprises a material selected from the group consisting of a solvent, a gelling agent, stabilizer and an anti-irritant.

17. The device of claim 10 wherein the adhesive overlay is nonocclusive and the backing layer is occlusive.

18. A device for administering an active agent to the skin or mucosa of an individual comprising a laminated composite of:

(a) a backing layer defining an upper portion of a reservoir and extending to the periphery of a peel seal disk;

(b) an active agent-permeable membrane extending to the periphery of the peel seal disk and the backing layer, and underlying the backing layer and membrane defining (c) the reservoir therebetween that contains a formulation of an active agent;

(d) the peel seal disc underlying an active agent-permeable membrane;

(e) a heat seal about the periphery of the peel seal disc, the active agent-permeable membrane and the backing layer;

(f) an adhesive overlay having a central portion overlying the backing layer and a peripheral portion that extends beyond the periphery of the peel seal disc;

(g) a removable release liner underlying the peripheral portion of the adhesive overlay and the peel seal disc; and (h) a tab on said peel seal disc to aid in removal of said disc.

19. The device of claim 18 including an adhesive layer that underlies the peripheral portion of the adhesive overlay and the peel seal disc and overlies the release liner.

20. The device of claim 18 wherein the adhesive overlay is nonocclusive and the backing layer is occlusive.

* * * * *

UNITED STATES PATENT AND TRADEMARK OFFICE
CERTIFICATE OF CORRECTION

PATENT NO. : 5,662,925
DATED : September 2, 1997
INVENTOR(S) : Charles D. Ebert, Werner Heiber, William R. Good, Srinivasan It is certified that error appears in the above-identified patent and that said Letters Patent is hereby corrected as shown below:

Column 4, line 67 the word "4,031,8943" should be --4,031,894--

Column 7, line 51 the word "w/v)" should be --(w/v)--

Signed and Sealed this

Twenty-fifth Day of November, 1997

Attest:

BRUCE LEHMAN

Attesting Officer

Commissioner of Patents and Trademarks